(12) United States Patent
Adachi et al.

(10) Patent No.: US 7,995,423 B2
(45) Date of Patent: Aug. 9, 2011

(54) ULTRASOUND TRANSDUCER AND ULTRASOUND DIAGNOSTIC APPARATUS

(75) Inventors: Hideo Adachi, Iruma (JP); Katsuhiro Wakabayashi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 198 days.

(21) Appl. No.: 12/422,504

(22) Filed: Apr. 13, 2009

(65) Prior Publication Data

US 2009/0204004 A1 Aug. 13, 2009

Related U.S. Application Data

(63) Continuation of application No. PCT/JP2007/069831, filed on Oct. 11, 2007.

(30) Foreign Application Priority Data

Oct. 12, 2006 (JP) .................................. 2006-279238

(51) Int. Cl.
*A61B 8/13* (2006.01)
(52) U.S. Cl. ........................................................ 367/181
(58) Field of Classification Search .................. 367/181; 600/459
See application file for complete search history.

(56) References Cited

U.S. PATENT DOCUMENTS

| 2005/0177045 A1 | 8/2005 | Degertekin et al. |
| 2009/0204004 A1* | 8/2009 | Adachi et al. .................. 600/459 |

FOREIGN PATENT DOCUMENTS

| JP | 2004-503313 | 2/2004 |
| JP | 2006-122188 | 5/2006 |
| JP | 2006-122344 | 5/2006 |
| JP | 2006-198240 | 8/2006 |
| WO | WO 01/97562 A2 | 12/2001 |
| WO | WO 2005/077012 A2 | 8/2005 |
| WO | WO 2005/120360 A1 | 12/2005 |
| WO | WO 2006/046471 A1 | 5/2006 |
| WO | WO 2008044727 A1 * | 4/2008 |

* cited by examiner

*Primary Examiner* — Dan Pihulic
(74) *Attorney, Agent, or Firm* — Scully, Scott, Murphy & Presser, PC

(57) ABSTRACT

This invention includes a first electrode which is fixed on a base, a vibration film which is disposed to oppose the first electrode with an air and vacuum portion between the vibration film and the first electrode, a second electrode which is supported by the vibration film and is connected to a predetermined potential, a ferroelectric which is electrically connected to the first electrode, and a driving portion that applies, to the first electrode, a driving signal which is a monopulse voltage signal and whose polarity is reversed every time the driving signal is outputted.

13 Claims, 8 Drawing Sheets

ULTRASOUND TRANSDUCER AND ULTRASOUND DIAGNOSTIC APPARATUS

CROSS REFERENCE TO RELATED APPLICATION

This application is a continuation application of PCT/JP2007/069831 filed on Oct. 11, 2007 and claims benefit of Japanese Application No. 2006-279238 filed in Japan on Oct. 12, 2006, the entire contents of which are incorporate herein by this reference.

BACKGROUND OF THE INVENTION

1. Field of the Invention

The present invention relates to an ultrasound transducer of a capacitance type and an ultrasound diagnostic apparatus.

2. Description of the Related Art

An ultrasound diagnostic method for applying an ultrasound into a body cavity and visualizing and diagnosing a state in a body from an echo signal of the ultrasound is prevalent. One of ultrasound diagnostic apparatuses used for such an ultrasound diagnostic method is an ultrasound endoscope. An ultrasound endoscope has an ultrasound transducer at a distal end of an insertion portion to be introduced into a body cavity. An ultrasound transducer has a function of converting an electric signal into an ultrasound and transmitting the ultrasound into a body cavity and receiving an ultrasound reflected in the body cavity and converting the ultrasound into an electric signal.

Conventionally, a piezoelectric element made of, e.g., a ceramic piezoelectric material such as PZT (lead zilconate titanate) has been mainly used as an ultrasound transducer. In recent years, an ultrasound transducer of a capacitance type (Capacitive Micromachined Ultrasound Transducer; hereinafter referred to as a c-MUT) manufactured using a micromachining technique has received attention. A c-MUT is disclosed in, e.g., Japanese Patent Application Laid Open Publication No. 2004-503313.

A c-MUT is configured to include a pair of flat electrodes (parallel plate electrodes) opposed to each other across an air and vacuum portion. The c-MUT transmits and receives an ultrasound in response to vibration of a film (membrane) including one of the electrodes.

Patent Document 1: Japanese Patent Application Laid Open Publication No. 2004-503313

At the time of transmission, the c-MUT vibrates the membrane in response to a change in electrostatic attraction between the pair of electrodes caused by application of a voltage signal at a predetermined frequency across the electrodes and transmits an ultrasound.

At the time of reception, since the c-MUT converts an ultrasound signal into an electric signal based on a change in capacitance between the pair of electrodes need to be charged in advance. It is thus necessary for the c-MUT to apply a DC bias voltage across the pair of electrodes at the time of reception.

SUMMARY OF THE INVENTION

An ultrasound transducer according to the present invention includes a first electrode which is disposed on a substrate and is used to input and output a signal, a vibration film which is disposed above the first electrode with an air and vacuum portion between the vibration film and the first electrode, a second electrode which is disposed on the vibration film and is set to a ground potential, and a ferroelectric which is electrically connected to the first electrode.

DETAILED DESCRIPTION OF THE PREFERRED EMBODIMENTS

First Embodiment

Figure 1:
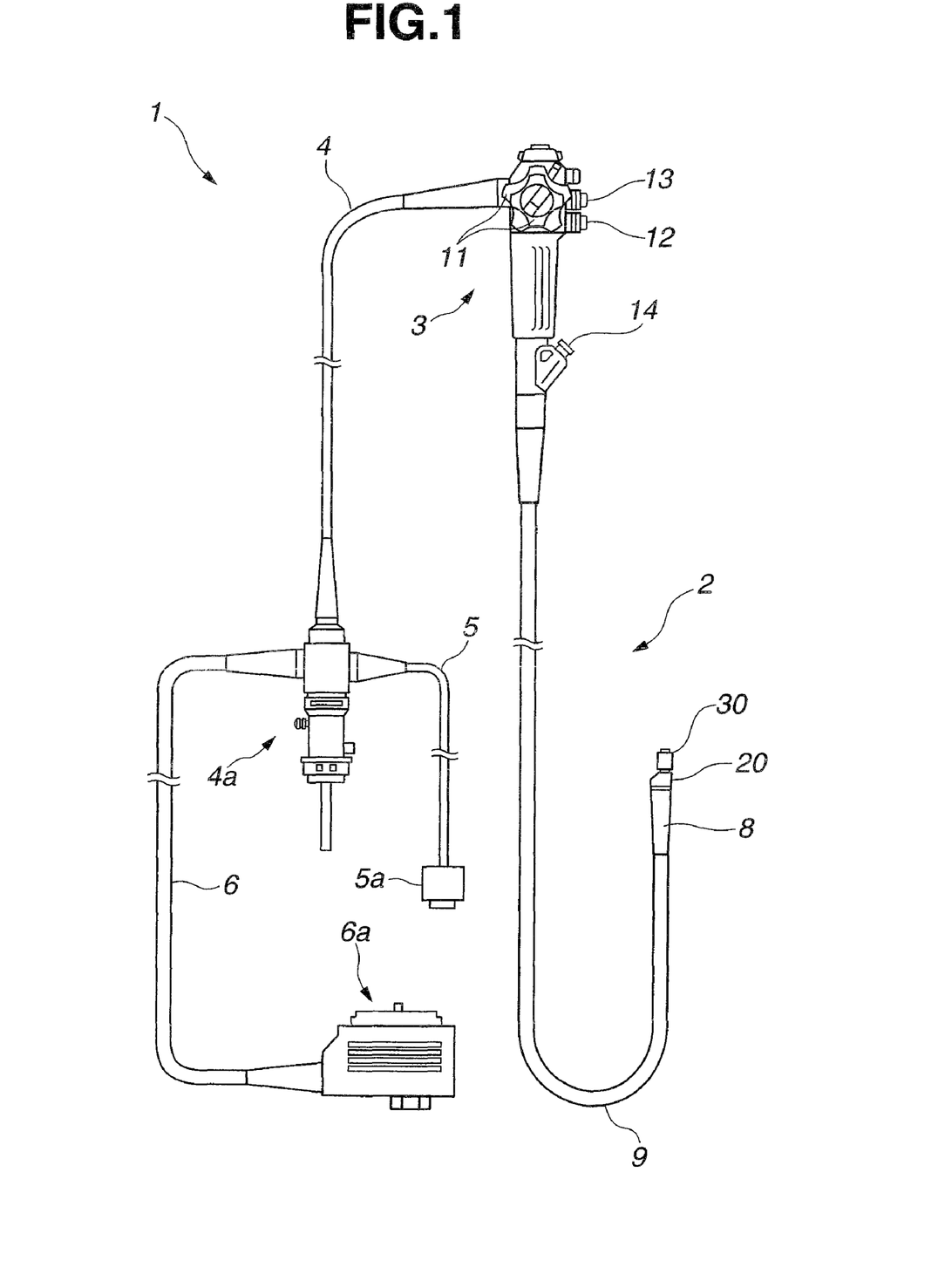
FIG. 1 is an explanatory view showing a schematic configuration of an ultrasound endoscope.
Figure 2:
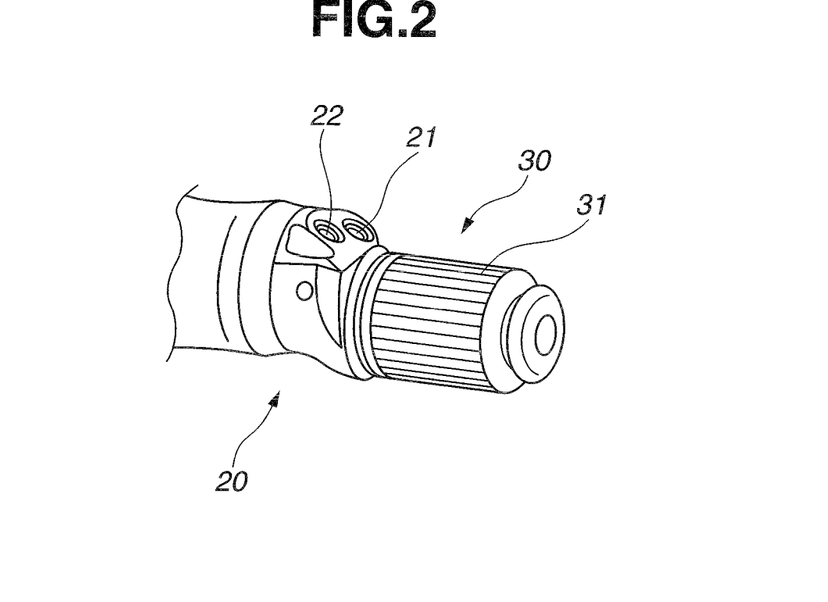
FIG. 2 is a perspective view showing a configuration of a distal end portion of the ultrasound endoscope.
Figure 3:
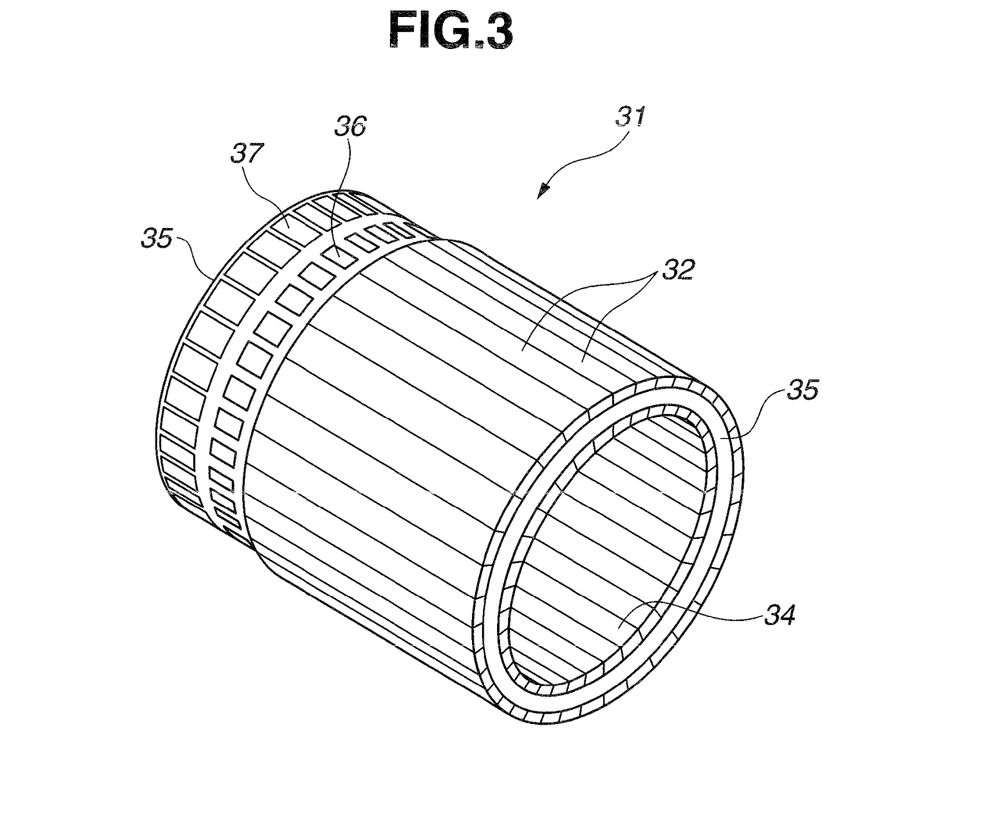
FIG. 3 is a perspective view of a transducer array.
Figure 4:
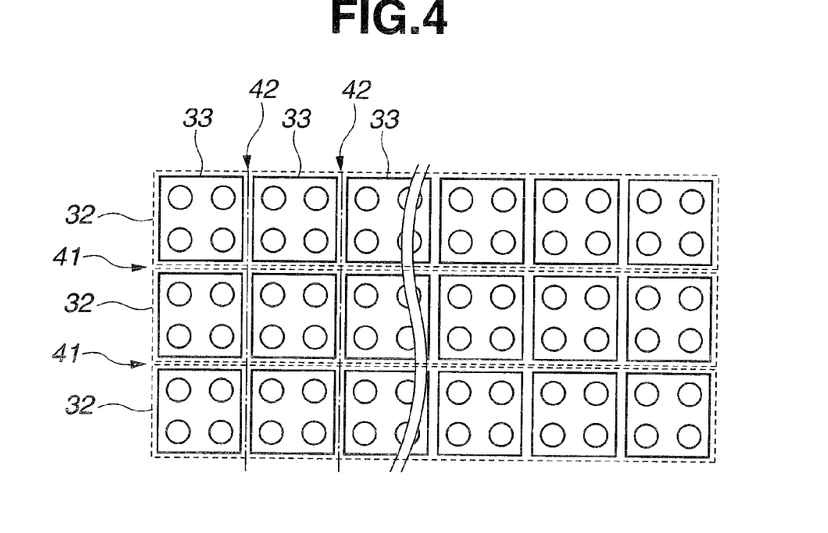
FIG. 4 is a top view of a transducer unit when viewed from an ultrasound transmission/reception direction.

A first embodiment of the present invention will be described below with reference to FIGS. 1 to 9. Note that, in the drawings used in the description below, members are shown at different scales such that each member is sized to be recognizable in the drawing. FIG. 1 is an explanatory view showing a schematic configuration of an ultrasound endoscope. FIG. 2 is a perspective view showing a configuration of a distal end portion of the ultrasound endoscope. FIG. 3 is a perspective view of a transducer array. FIG. 4 is a top view of a transducer unit when viewed from an ultrasound transmission/reception direction.

As shown in FIG. 1, an ultrasound endoscope 1 which is an ultrasound diagnostic apparatus according to the present embodiment is mainly composed of an elongated insertion portion 2 to be introduced into a body cavity, an operation portion 3 located at a proximal end of the insertion portion 2, and a universal cord 4 extending from a side of the operation portion 3.

An endoscope connector 4a to be connected to a light source apparatus (not shown) is provided at a proximal end portion of the universal cord 4. An electric cable 5 to be detachably connected to a camera control unit (not shown) via an electric connector 5a and an ultrasound cable 6 to be detachably connected to an ultrasound observation apparatus (not shown) via an ultrasound connector 6a are extending from the endoscope connector 4a.

The insertion portion 2 is composed of a distal end rigid portion 20 made of a rigid resin member, a bendable bending portion 8 located at a rear end of the distal end rigid portion 20, and a thin and long tube portion 9 with flexibility located at a rear end of the bending portion 8 and leading to a distal end portion of the operation portion 3 which are provided to be continuous in order from a distal end side of the insertion portion 2. An ultrasound transmission/reception portion 30 for transmitting and receiving an ultrasound, details of which will be described later, is provided on a distal end side of the distal end rigid portion 20.

An angle knob 11 for controlling to bend the bending portion 8 in a desired direction, an air supply/water supply button 12 for performing air supply and water supply operation, a suction button 13 for performing suction operation, a treatment instrument insertion port 14 serving as an inlet for a treatment instrument to be introduced into a body cavity, and the like are provided in the operation portion 3.

As shown in FIG. 2, an illumination lens (not shown) constituting an illumination optical portion which applies illumination light to an observation site, an objective lens 21 constituting an observation optical portion which captures an optical image of the observation site, a suction-cum-forceps port 22 serving as an opening via which an excised site is sucked in and from which a treat instrument is to project, and an air supply/water supply port (not shown) for air supply and water supply are provided at the distal end rigid portion 20.

As shown in FIG. 3, the ultrasound transmission/reception portion 30 provided at a distal end of the distal end rigid portion 20 is configured to include a transducer array 31, driving circuits 34, and a FPC 35. The FPC 35 is a wiring board (flexible wiring board) which has flexibility and has mounting surfaces formed on two surfaces. In the ultrasound transmission/reception portion 30, the FPC 35 is disposed to be almost cylindrically wound about an axis almost parallel to an insertion axis of the distal end rigid portion 20.

The transducer array 31 serving as a two-dimensional ultrasound transducer array is provided on an outer peripheral surface of the cylindrical FPC 35. The transducer array 31 is configured to include a plurality of transducer units 32 circumferentially arrayed on the outer peripheral surface of the FPC 35. The transducer units 32 each have an almost rectangular shape when viewed from a normal direction of the outer peripheral surface of the cylindrical FPC 35 and are equally spaced in a circumferential direction as a lateral direction on the outer peripheral surface of the cylindrical FPC 35. The transducer array 31 is composed of, e.g., several tens to several hundreds of transducer units 32. The transducer array 31 according to the present embodiment includes 128 transducer units 32.

As shown in FIG. 4, each transducer unit 32 is composed of a plurality of arrayed transducer elements 33. In the present embodiment, the transducer elements 33 each have an almost square shape when viewed from the normal direction of the outer peripheral surface of the FPC 35 and are one-dimensionally arrayed in a longitudinal direction of the transducer unit. In the present embodiment, each transducer unit 32 is composed of 64 transducer elements 33.

Each transducer element 33 is composed of a plurality of transducer cells serving as ultrasound transducers according to the present embodiment, details of which will be described later. In a single transducer element 33, the transducer cells 100 are all electrically connected in parallel and, upon receipt of a driving signal from the ultrasound observation apparatus, simultaneously transmit in-phase ultrasound. That is, in the present embodiment, one transducer element 33 serves as a minimum driving unit for transmitting and receiving an ultrasound. In the present embodiment, each transducer element 33 is composed of four transducer cells 100.

A transducer unit boundary groove 41 serving as a groove portion which separates the transducer units 32 from each other is formed between each adjacent two of the transducer units 32. A transducer element boundary groove 42 serving as a groove portion which separates the transducer elements 33 from each other is formed between each adjacent two of the transducer elements 33. The above described formation of groove portions around a circumference of each transducer element 33 serving as the minimum driving unit allows a reduction in crosstalk between each adjacent two of the transducer elements 33.

Each transducer element 33 transmits an ultrasound in a normal direction of one of the mounting surfaces of the FPC 35, i.e., in a radially outward direction of the cylindrical FPC 35. Accordingly, each transducer unit 32 composed of the one-dimensionally arrayed transducer elements 33 constitutes a one-dimensional ultrasound transducer array, and the plurality of arrayed transducer units 32 constitute the transducer array 31, which is a two-dimensional ultrasound transducer array.

The plurality of driving circuits 34 are mounted on an inner peripheral surface of the cylindrical FPC 35, i.e., on the mounting surface opposite to the mounting surface where the transducer array 31 is mounted. Each driving circuit 34 has electric circuits such as a pulsar for driving the transducer elements 33 and a selection circuit and is electrically connected to the individual transducer elements 33.

The driving circuits 34 are electrically connected to a plurality of signal electrodes 36 and a plurality of ground electrodes 37 which are formed on the outer peripheral surface of the cylindrical FPC 35. Note that although each signal electrode 36 is shown as one electrode in FIG. 3, the signal electrode 36 is divided into signal electrodes equal in number to the corresponding transducer elements 33, and one signal electrode is provided for each transducer element 33.

One end of a coaxial cable which is inserted through the ultrasound cable 6 and whose other end is electrically connected to the ultrasound connector 6a is electrically connected to the signal electrodes 36 and ground electrodes 37. The driving circuit 34 is thus electrically connected to the ultrasound observation apparatus.

The ultrasound transmission/reception portion 30 with the above-described configuration simultaneously or alternately performs so-called electronic radial scanning for radially transmitting and receiving an ultrasound on a plane almost orthogonal to the insertion axis of the distal end rigid portion 20 and so-called electronic sector scanning for radially transmitting and receiving an ultrasound on a plane including the insertion axis of the distal end rigid portion 20, by means of the transducer array 31 serving as the two-dimensional ultrasound transducer array disposed on the outer peripheral surface of the cylindrical FPC 35. That is, the ultrasound endoscope 1 according to the present embodiment is capable of three-dimensional ultrasound scanning in a body cavity.

Figure 5:
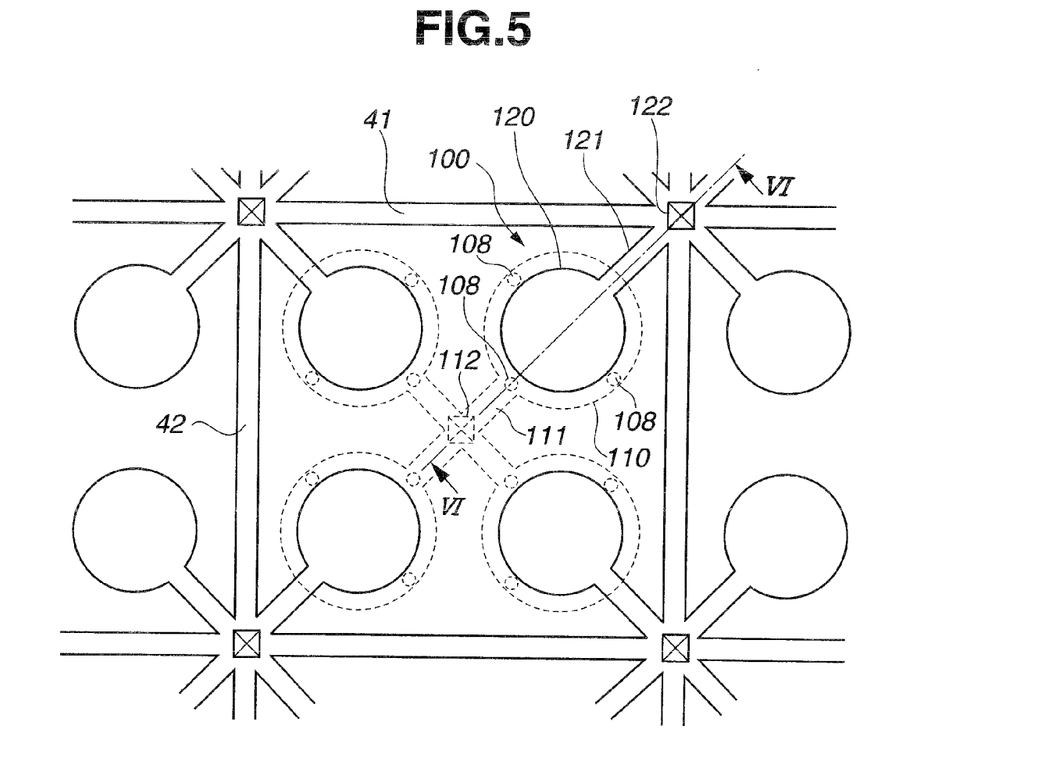
FIG. 5 is a top view of a transducer cell.
Figure 6:
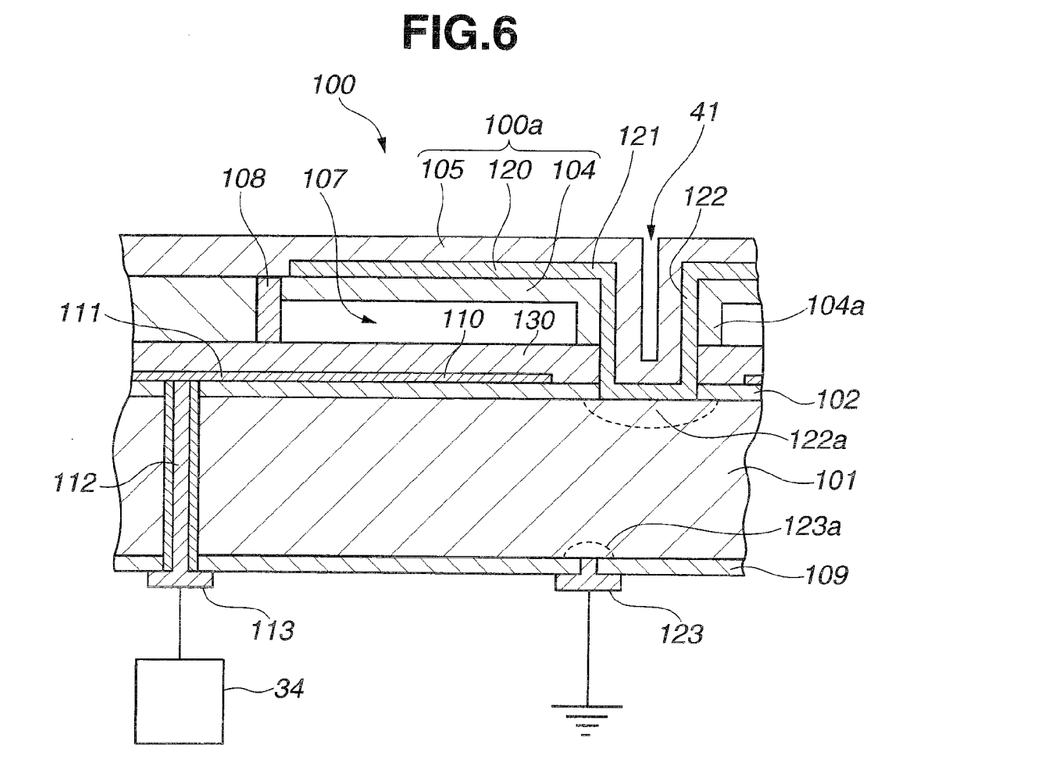
FIG. 6 is a sectional view taken along line VI-VI of FIG. 5.
Figure 7:
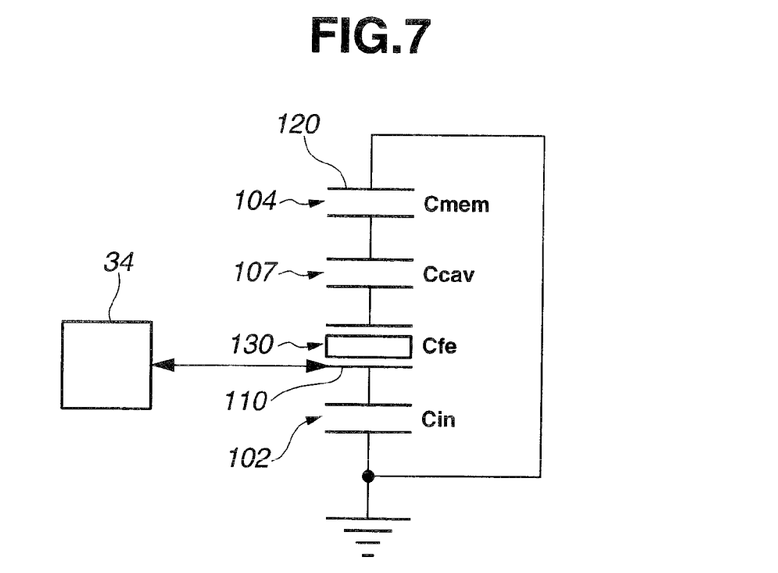
FIG. 7 is an equivalent circuit diagram of the transducer cell.

A configuration of the transducer cell 100 as an ultrasound transducer of a capacitive type according to the present embodiment will be described below. FIG. 5 is a top view of the transducer cell 100. FIG. 6 is a sectional view taken along line VI-VI of FIG. 5. FIG. 7 is an equivalent circuit diagram of the transducer cell 100.

The transducer cell 100 according to the present embodiment is within technical scope of so-called MEMS (Micro Electro Mechanical Systems). The transducer cell 100 is an ultrasonic transducer of a capacitance type formed on a silicon substrate 101 (base) made of a low-resistivity silicon semiconductor by a micromachining technique and is referred to as a c-MUT (Capacitive Micromachined Ultrasonic Transducer). In the present embodiment, the transducer cell 100 is composed of parallel plate electrodes formed using a semiconductor process and has a layered structure formed in layers on the silicon substrate 101.

Note that, as for a vertical positional relationship among respective layers, a direction away from a surface of the silicon substrate 101 in a normal direction is assumed as an upward direction, in a following explanation of the layered structure. For example, in the sectional view in FIG. 6, an upper electrode 120 is described as being disposed above a lower electrode 110. A thickness of each layer means a dimension of the layer in a direction parallel to a normal line of the surface of the silicon substrate 101. In a following description, of surfaces of the silicon substrate 101, a surface where the transducer cells 100 are formed will be referred to as a cell formation surface, and a surface opposite to the surface where the transducer cells 100 are formed will be referred to as a back surface, for the sake of convenience.

The transducer cell 100 is configured to include the lower electrode 110 (a first electrode) and the upper electrode 120 (a second electrode), which are a pair of parallel plate electrodes facing each other with an almost cylindrical air and vacuum portion, a cavity 107, between the electrodes. The transducer cell 100 transmits and receives an ultrasound by vibration of a membrane 100a (a vibration film) which is an elastic film-like structure including the upper electrode.

A structure of the transducer cell 100 according to the present embodiment will be described in detail below.

The silicon substrate 101 is composed of a low-resistivity silicon wafer with conductivity. A first insulating film 102 and a back insulating film 109 which are electrically insulative silicon oxide films are respectively formed on the two surfaces of the silicon substrate 101. The first insulating film 102 and back insulating film 109 are thermal oxide films formed by thermally oxidizing the silicon substrate 101.

The lower electrode 110, which is an almost circular conductive layer when viewed from above, is formed on the cell formation surface, i.e., the first insulating film 102 of the silicon substrate 101. The lower electrode 110 is formed by forming a Mo (molybdenum) film by sputtering and patterning the Mo film. As for the lower electrode 110, four lower electrodes 110 adjacent to each other when viewed from above are electrically connected by almost X-shaped wiring 111 leading from the lower electrodes 110.

A material for forming the lower electrode 110, which is a lowermost layer portion of a layered structure and is formed on the silicon oxide film, other than Mo, is desirably a high-melting point metal such as W (tungsten), Ti (titanium), and Ta (tantalum) or an alloy of the metals. The material, however, is not limited to the metals and alloys and may be Al (aluminum), Cu (copper), or the like as long as high-temperature heat treatment can be avoided in a later manufacturing process. The lower electrode 110 may have a multilayered structure in which two or more types of conductive materials are stacked.

A wafer through electrode 112 which is formed to vertically extend through the silicon substrate 101 is provided at a wiring intersection of the wiring 111, which is almost X-shaped when viewed from above and is leading from the lower electrodes 110, for each transducer element 33. The wafer through electrode 112 is electrically insulated from the silicon substrate 101 and is electrically connected to a signal input/output electrode pad 113 which is formed on the back insulating film 109.

In other words, the lower electrode 110 is electrically connected to the signal input/output electrode pad 113 formed on the back surface of the silicon substrate 101 via the wiring 111 leading from the lower electrodes 110 and the wafer through electrode 112.

A ferroelectric film 130 made of a ferroelectric is formed on the lower electrode 110. A ferroelectric has the property that spontaneous polarization is present, and a direction of the spontaneous polarization is reversed by an electric field and characteristically has hysteresis characteristics (ferroelectricity). In the present embodiment, the ferroelectric film 130 is preferably composed of a bismuth layer structured ferroelectric material (BLSF) represented by $(Bi_2O_2)^{2+}$. $(A_{m-1}B_mO_{3m+1})^{2-}$ such as $SrBi_2TaO_9$ (m=2) or $Sr_2Bi_4Ti_5O_{18}$ (m=5) and is formed by CVD, sputtering, sol-gel spin coating, or the like.

A Bi layer structured ferroelectric which is a material for forming the ferroelectric film 130 is a material which is little degraded by repeated polarization reversal. Note that a ferroelectric for forming the ferroelectric film 130 is not limited to a Bi layer structured ferroelectric.

A second insulating film 104 which is electrically insulative is formed on the ferroelectric film 130 via the cavity 107. In the present embodiment, the second insulating film 104 is a silicon nitride film and is formed by LPCVD, plasma CVD, or the like. Note that the second insulating film 104 may be a silicon oxide film.

The cavity 107, which is a closed air and vacuum portion under ambient pressure or reduced pressure is formed between the ferroelectric film 130 and the second insulating film 104. The cavity 107 has an almost cylindrical shape and is provided almost concentrically relative to the lower electrode 110 when viewed from above.

In the present embodiment, the cavity 107 is formed by sacrificial layer etching, which is a known technique. Sacrificial layer removing holes for causing the cavity 107 and a layer on the second insulating film 104 to communicate with each other which are used for the sacrificial layer etching are sealed with plugs 108. The sacrificial layer removing holes are formed at three positions on a circumference of the cavity 107. Note that the cavity 107 may be formed by a method of bonding together wafers after microprocessing.

The upper electrode 120, which is a conductive layer with an almost circular shape when viewed from above, is formed on the second insulating film 104. The upper electrode 120 is provided almost concentrically relative to the lower electrode 110 when viewed from above, i.e., at a position opposed to the lower electrode 110. In the present embodiment, the upper electrode 120 is formed by forming a Al film by sputtering and patterning the Al film.

As for the upper electrode 120, four upper electrodes 120 adjacent to each other when viewed from above are electrically connected by almost X-shaped wiring 121 leading from the upper electrodes 120. The wiring 121 leading from the upper electrodes 120 is disposed to minimize a part of the wiring 121 which overlaps with the above-described wiring 111 leading from the lower electrodes 110 when viewed from above. Arranging the wiring 111 leading from the lower electrodes 110 and the wiring 121 leading from the upper electrodes 120 in the above-described manner to minimize an overlap makes it possible to reduce generation of parasitic capacitance in a wiring portion.

Note that any conductive material other than Al, such as Cu, W, Mo, Ti, or Ta, may be used as a material for forming the upper electrode 120. The upper electrode 120 may have a multilayered structure in which two or more types of conductive materials are stacked.

A wiring intersection of the wiring 121 leading from the upper electrodes 120, which is almost X-shaped when viewed from above, is formed at the transducer unit boundary groove 41. The transducer unit boundary groove 41 is formed to vertically extend through a membrane support portion 104a of the second insulating film 104 and reach the silicon substrate 101. In the transducer unit boundary groove 41, a through electrode 122 is formed in one and the same process for the upper electrode 120 and the wiring 121 leading from the upper electrodes 120. The through electrode 122 is electrically connected to the silicon substrate 101 via an ohmic contact region 122a.

A ground electrode pad 123 is formed on the back insulating film 109. The ground electrode pad 123 is electrically connected to the silicon substrate 101 via an ohmic contact region 123a.

In other words, the upper electrode 120 is electrically connected to the ground electrode pad 123 formed on the back surface of the silicon substrate 101 via the wiring 121 leading from the upper electrodes 120, the through electrode 122, and the silicon substrate 101.

An upper protective film 105 which is electrically insulative is formed on the upper electrode 120. In the present embodiment, the upper protective film 105 is a silicon nitride film and is formed by plasma CVD. Note that the upper protective film 105 may be made of a silicon oxide film, hafnium nitride (HfN), hafnium oxide nitride (HfON), or the like, instead of a silicon nitride. In particular, HfN and HfON are preferable for a protection film because a high-density film is obtained.

Although not shown, a film made of, e.g., a paraxylylene resin which has water resistance, chemical resistance, and the like and is excellent in biocompatibility and electrical insulation may be formed on the upper protective film 105.

The transducer element 33 including the transducer cells 100 with the above-described configuration is mounted on the FPC 35 by a known method such as solder bonding, anisotropic conductive film bonding, or ultrasound bonding. Accordingly, the transducer cell 100 is electrically connected to the driving circuit 34 mounted on an opposite side of the FPC 35 via the signal input/output electrode pad 113 and ground electrode pad 123.

In other words, transmission and reception of a driving signal which is a voltage signal and a received signal are performed between the lower electrode 110 and the driving circuit 34. The ground electrode pad 123 is set to a ground potential, and the upper electrode 120 is connected to the ground potential via the silicon substrate 101 and ground electrode pad 123.

As described above, in the present embodiment, the low-resistivity silicon substrate 101 is used as a substrate on which the transducer cells 100 are to be formed, and the silicon substrate 101 is set to the ground potential. This makes it possible to block noise coming from a back surface side and obtain an ultrasound image with a higher S/N ratio.

The provision of the signal input/output electrode pad 113 and ground electrode pad 123 on a back surface side of the transducer cell 100 allows a reduction in mounting area.

In the above-described configuration, the lower electrode 110, upper electrode 120, and cavity 107 each have an almost circular shape when viewed from above. However, shapes of the components are not limited to the shapes in the present embodiment and may be, e.g., equilateral hexagonal or rectangular. Dimensions of the membrane 100a and cavity 107 are determined by a wavelength and power of an ultrasound used at the time of observation.

Figure 8:
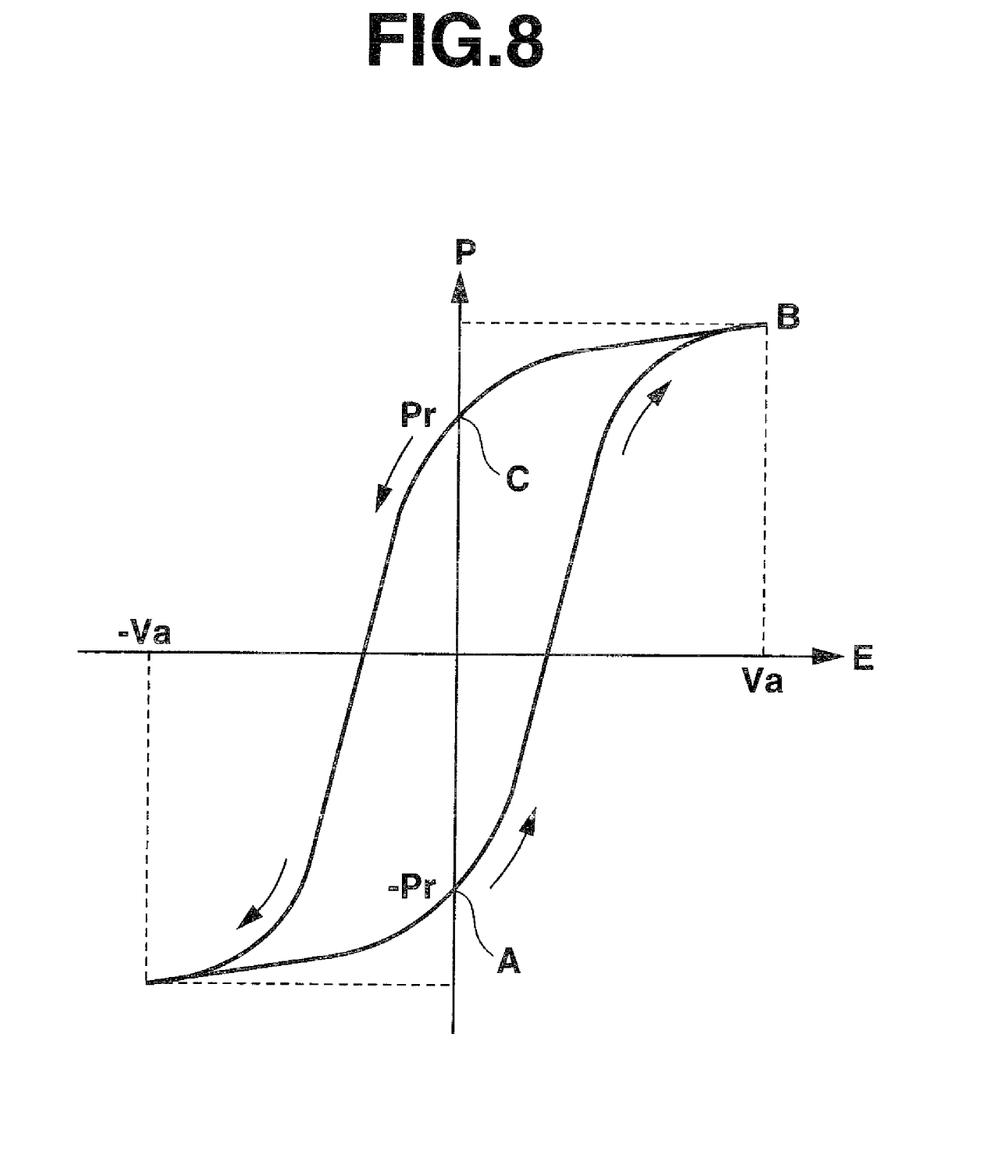
FIG. 8 is a graph for explaining a polarization hysteresis characteristic of a ferroelectric.
Figure 9:
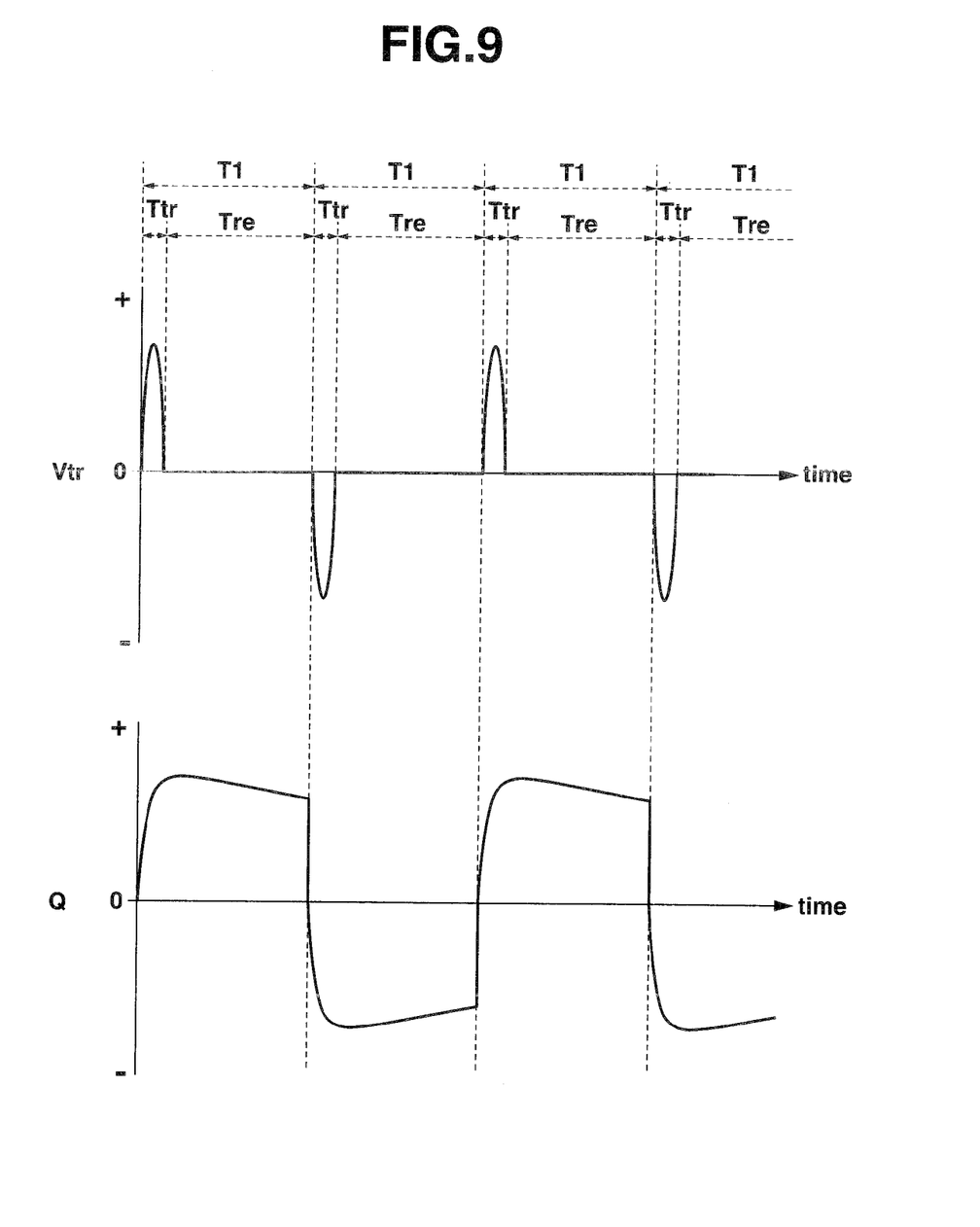
FIG. 9 is a timing chart for explaining a method for driving the transducer cell.

A driving method for and operation of the ultrasound endoscope 1 and transducer cell 100 with the above-described configuration will be described below. FIG. 7 is an equivalent circuit diagram of the transducer cell according to the present embodiment. FIG. 8 is a graph for explaining a polarization hysteresis characteristic (P-E hysteresis loop) of a ferroelectric. FIG. 9 is a timing chart for explaining driving of the transducer cell.

The ferroelectric film 130 will be described below as having polarization hysteresis as shown in FIG. 8. In FIG. 8, an abscissa represents a voltage E applied to the ferroelectric film 130 while an ordinate represents a polarization quantity P of the ferroelectric film 130. The polarization quantity P is a value showing an extent to which electric charges are polarized in the ferroelectric film 130.

In FIG. 8, reference characters Pr denote a residual polarization, and the residual polarization Pr is a value showing an extent to which electric charges remaining in the ferroelectric film 130 are polarized when the applied voltage E is set to 0. Since each polarized electric charge remaining in the ferroelectric film 130 when no voltage is applied is neutralized with an electric charge with an opposite polarity located near a surface of the ferroelectric film 130, the polarization of the electric charges cannot be observed from an outside. However, a change in a voltage applied to the ferroelectric film 130 or a change in a temperature or pressure applied to the ferroelectric film 130 causes a change in the quantity of polarized charge in the ferroelectric film 130. A balance of electric charges in a neutralized state is disturbed, and electric charges left unneutralized appear on the surface of the ferroelectric film 130.

In the equivalent circuit diagram of FIG. 7, an equivalent capacitance of the membrane 100a is represented by Cmem, an equivalent capacitance of the cavity 107 is represented by Ccav, an equivalent capacitance of the ferroelectric film 130 is represented by Cfe, and an equivalent capacitance of the first insulating film 102 is represented by Cin.

In FIG. 9, an abscissa represents time, an ordinate Vtr represents a voltage of a driving signal, and an ordinate Q represents the quantity of electric charge on the lower electrode.

In the present embodiment, a driving signal which is a voltage signal outputted from the driving circuit 34 serving as a driving portion is applied to the lower electrode 110, as shown in FIG. 7. if a divided voltage across Cmem, Ccav, and Cfe is higher than a polarization reversal voltage of the ferroelectric film 130 when a driving signal is inputted to the lower electrode 110, a polarization reversal occurs, and a polarization reversal charge is induced.

For example, assume that polarization of the ferroelectric film 130 is in a state A (with a polarization quantity of −Pr) shown in FIG. 8. When a voltage of +Va or more is applied to the ferroelectric film 130, the polarization of the ferroelectric film 130 reaches a state B. After that, the polarization of the ferroelectric film 130 enters a state C (with a polarization quantity of Pr) and is reversed.

In the ultrasound endoscope 1 according to the present embodiment, the transducer cell 100 is driven by the driving circuit 34 such that the transducer cell 100 repeats an operation of transmitting an ultrasound during a transmission period Ttr and receiving an ultrasound during a reception period Tre after the transmission period Ttr for each transmission/reception period T1 which is a predetermined period.

As shown in FIG. 9, the driving circuit 34 outputs a half-wave pulse voltage signal (monopulse voltage signal) to the lower electrode 110 only once during one transmission period Ttr. A polarity for a half-wave pulse voltage signal outputted from the driving circuit 34 is reversed every time a half-wave pulse voltage signal is outputted. A voltage value of a half-wave pulse voltage signal is set to a value which is sufficiently high to cause a polarization reversal in the ferroelectric film 130 and makes ultrasound power generated by vibration of the membrane 100a sufficiently high.

That is, a polarity for a driving signal applied to the lower electrode 110 is reversed every time a driving signal is inputted. For the reason, every time one driving signal is inputted, a polarization reversal of the ferroelectric film 130 occurs, and electric charges with a charge quantity of 2Pr (=Pr-(−Pr)) are induced on the lower electrode 110. The electric charges induced on the lower electrode 110 are held until a next driving signal is inputted, as shown in FIG. 9.

The transducer cell 100 according to the present embodiment is driven by the above-described driving method and operates in a manner below.

First, a driving signal which is a half-wave pulse voltage signal is inputted to the lower electrode 110 of the transducer cell 100 during a transmission period Ttr. Upon the input of the driving signal, a potential difference between the lower electrode 110 and the upper electrode 120 changes, and electrostatic attraction between the two electrodes varies, thus resulting in a change in a distance between the two electrodes. That is, the membrane 100a vibrates, thereby transmitting an ultrasound.

Note that, as described in detail by the present applicant in Japanese Patent Application No. 2004-172970, a DC bias voltage may be applied in pulses across the lower electrode 110 and the upper electrode 120 only during a transmission period Ttr. The application of a DC bias voltage across the lower electrode 110 and the upper electrode 120 at the time of ultrasound transmission achieves favorable effects such as an increase in a bandwidth of an ultrasound to be transmitted and an increase in sound pressure.

The input of the driving signal to the lower electrode 110 during the transmission period Ttr causes a polarization reversal of the ferroelectric film 130 and induces electric charges on the lower electrode 110. The charges cause a DC voltage to be applied across the lower electrode 110 and the upper electrode 120. That is, during a reception period Tre following the transmission period Ttr, the DC bias voltage remains applied across the lower electrode 110 and the upper electrode 120.

During the reception period Tre, an ultrasound reflected in a body cavity reaches the transducer cell 100, and the reflected wave vibrates the membrane 100a. For the reason, a capacitance between the lower electrode 110 and the upper electrode 120 changes in response to a change in a distance between the lower electrode 110 and the upper electrode 120. Since the DC bias voltage is applied across the lower electrode 110 and the upper electrode 120, the quantity of electric charge on the lower electrode 110 varies in response to the change in the capacitance between the lower electrode 110 and the upper electrode 120. That is, the ultrasound observation apparatus is capable of receiving an ultrasound by measuring, as a received signal, a change in the quantity of electric charge on the lower electrode 110 of the transducer cell 100.

As described above, the provision of the ferroelectric film 130 allows the transducer cell 100 according to the present embodiment to realize operation equivalent to operation of a conventional c-MUT requiring application of a DC bias voltage. That is, the transducer cell 100 according to the present embodiment does not require application of a DC bias voltage and is capable of transmitting and receiving an ultrasound only using a pulse signal. It is thus possible to make a voltage effective value required for driving lower than the conventional c-MUT.

Therefore, the transducer cell 100 according to the present embodiment is capable of transmitting and receiving an ultrasound with lower power consumption and suppressing a burden on wiring. Since wiring and a circuit for applying a DC bias voltage are unnecessary for the ultrasound endoscope 1 including the above-described transducer cell 100, it is possible to achieve further miniaturization of the device.

According to the ultrasound endoscope 1 including the transducer cell 100 of the present embodiment, since the transducer cell 100 does not contain a toxic substance such as lead, unlike piezoelectric ceramic, it is possible to realize a diagnostic apparatus with a small environmental burden.

In the present embodiment, a driving signal for driving the transducer cell 100 is applied to a lower layer side of the transducer cell 100, i.e., the lower electrode 110 located on a side opposite to a direction in which an ultrasound is transmitted and received to and from an observation object. The upper electrode 120 disposed at a position nearer to the observation object than the lower electrode 110 is connected to the ground potential. That is, only the conductive layer connected to the ground potential is provided at an outer peripheral portion of the transducer cell 100 according to the present embodiment while the conductive layer to which a driving signal is applied is disposed only on an inner side of the transducer cell 100. Accordingly, electrical insulation between the conductive layer to which a driving signal is applied and an outside can be reliably and easily ensured. Additionally, as described above, wiring or the like for applying a DC bias voltage with a high effective value is unnecessary. For example, it is thus possible to reduce a thickness of the protective film for covering the transducer cell 100 and achieve miniaturization of the device.

Note that although the driving circuit 34 for driving the transducer cell 100 is formed separately from the transducer cell 100 and is mounted on the FPC 35 in the above-described embodiment, the present invention is not limited to this.

For example, in the present embodiment, the transducer cell 100 is formed on the silicon substrate 101 made of a silicon semiconductor, and it is possible to monolithically form at least a part of the electronic circuit for driving the transducer cell 100 on the silicon substrate 101. Forming the driving circuit on the silicon substrate 101 in the above-described manner makes it possible to eliminate a process of separately mounting the driving circuit and thereby reduce the number of processes. It is also possible to improve reliability of electrical connection between the driving circuit and the transducer cell 100.

Second Embodiment

Figure 10:
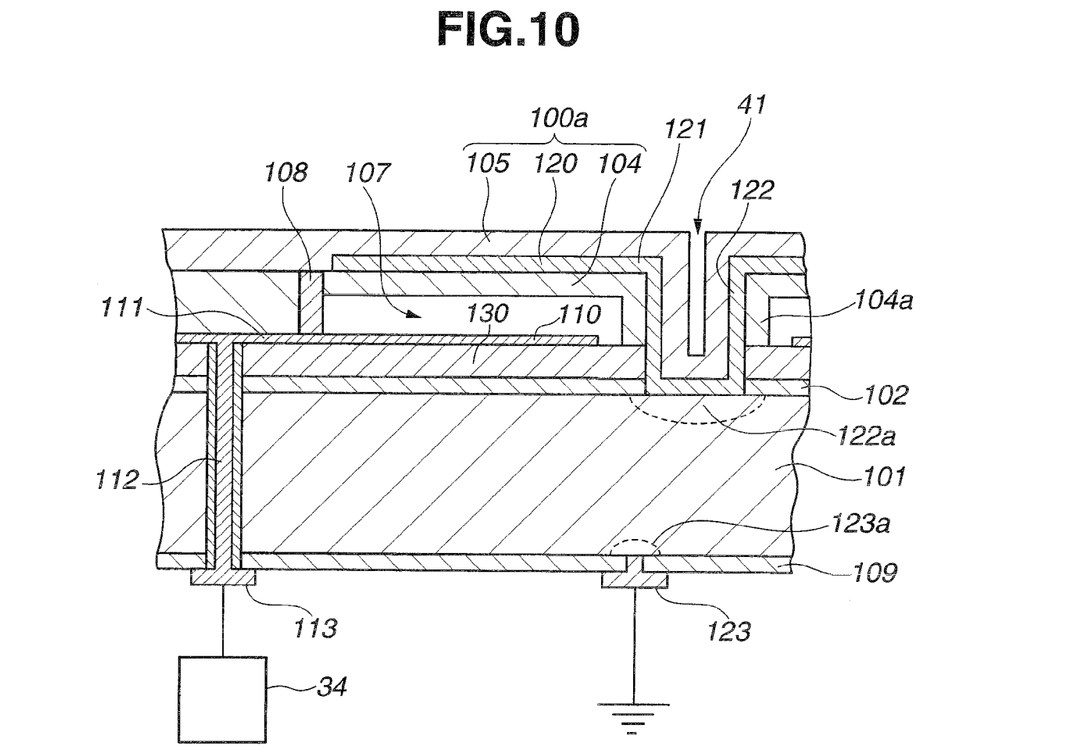
FIG. 10 is a sectional view of a transducer cell according to a second embodiment.
Figure 11:
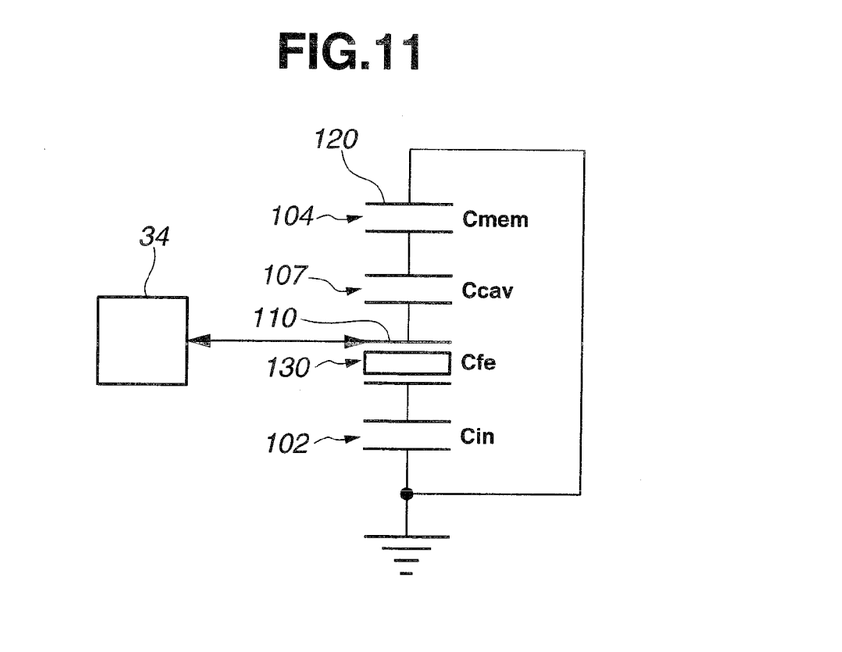
FIG. 11 is an equivalent circuit diagram of the transducer cell according to the second embodiment.

A second embodiment of the present invention will be described below with reference to FIGS. 10 and 11. FIG. 10 is a sectional view of a transducer cell according to the second embodiment. FIG. 11 is an equivalent circuit diagram of a transducer cell 100 according to the second embodiment.

The second embodiment is different from the configuration in the first embodiment only in placement of a ferroelectric film 130. Thus, only the difference will be described below. Same components as the components in the first embodiment are denoted by same reference numerals, and a description of the components will be appropriately omitted.

In the transducer cell according to the present embodiment, the ferroelectric film 130 is provided on a lower layer side of a lower electrode 110, as shown in FIG. 10.

A driving method for the transducer cell according to the present embodiment is same as the driving method in the first embodiment. However, a driving signal outputted from a driving circuit 34 serving as a driving portion and applied to the lower electrode 110 is set to have a value which makes a divided voltage across an equivalent capacitance Cfe of the ferroelectric film 130 and an equivalent capacitance Cin of a first insulating film 102 higher than a polarization reversal voltage of the ferroelectric film 130.

Since a drop in a voltage applied to the ferroelectric film 130 due to voltage division is smaller in the present embodiment than in the first embodiment, a voltage effective value of a driving signal applied to the lower electrode 110 can be made lower than the voltage effective value in the first embodiment. Accordingly, according to the present embodiment, it is possible to provide a preferred ultrasound transducer in a form which is used in a body cavity.

According to the present embodiment, since the voltage effective value of the driving signal can be made lower than the voltage effective value in the first embodiment, a value of a current flowing through the driving circuit or wiring becomes lower, and power consumption can be reduced. This allows further miniaturization of the driving circuit and makes it possible to prevent characteristics of the transducer cell from varying due to heat generation of the driving circuit.

According to the present embodiment, since the ferroelectric film 130 is not disposed between the lower electrode 110 and an upper electrode 120, it is possible to reduce a distance between the lower electrode 110 and the upper electrode 120 (an inter-electrode distance) as compared with the first embodiment.

Therefore, according to the present embodiment, capacitance between electrodes can be increased, a higher sound pressure of an ultrasound to be transmitted is obtained, and an ultrasound transducer of a capacitance type with higher sensitivity can be realized.

Third Embodiment

Figure 12:
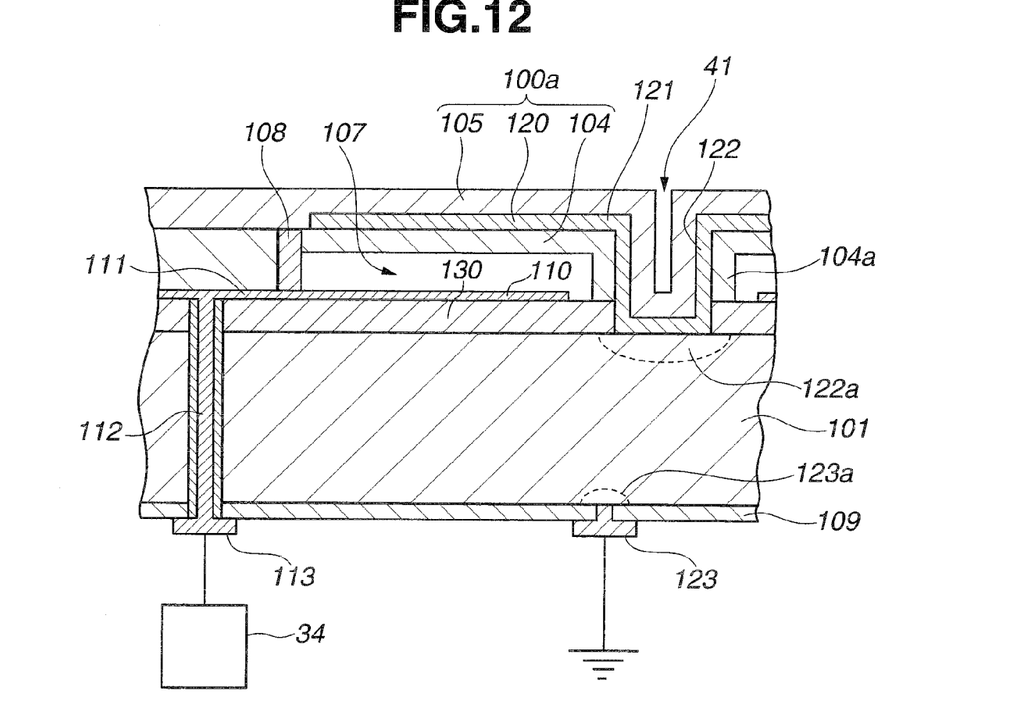
FIG. 12 is a sectional view of a transducer cell according to a third embodiment.

A third embodiment of the present invention will be described below with reference to FIG. 12. FIG. 12 is a sectional view of a transducer cell according to the third embodiment. The third embodiment is different from the configuration in the second embodiment only in placement of a ferroelectric film 130. Thus, only the difference will be described below. Same components as the components in the first embodiment are denoted by same reference numerals, and a description of the components will be appropriately omitted.

In the transducer cell according to the present embodiment, a first insulating film is not formed on a silicon substrate 101, the ferroelectric film 130 is disposed on the silicon substrate 101, and a lower electrode 110 is further disposed on the ferroelectric film 130, as shown in FIG. 12.

According to the present embodiment, a drop in a voltage applied to the ferroelectric film 130 due to voltage division is small as compared with the second embodiment. Thus, a voltage effective value of a driving signal applied to the lower electrode 110 can be made further lower. Accordingly, according to the present embodiment, it is possible to provide a preferred ultrasound transducer in a form which is used in a body cavity.

According to the present embodiment, since the voltage effective value of the driving signal can be made lower than the voltage effective value in the second embodiment, a value of a current flowing through a driving circuit or wiring becomes lower, and power consumption can be reduced. This allows further miniaturization of the driving circuit and makes it possible to prevent characteristics of the transducer cell from varying due to heat generation of the driving circuit.

The absence of a first insulating film allows a reduction in the number of processes in a transducer cell manufacturing process.

Fourth Embodiment

Figure 13:
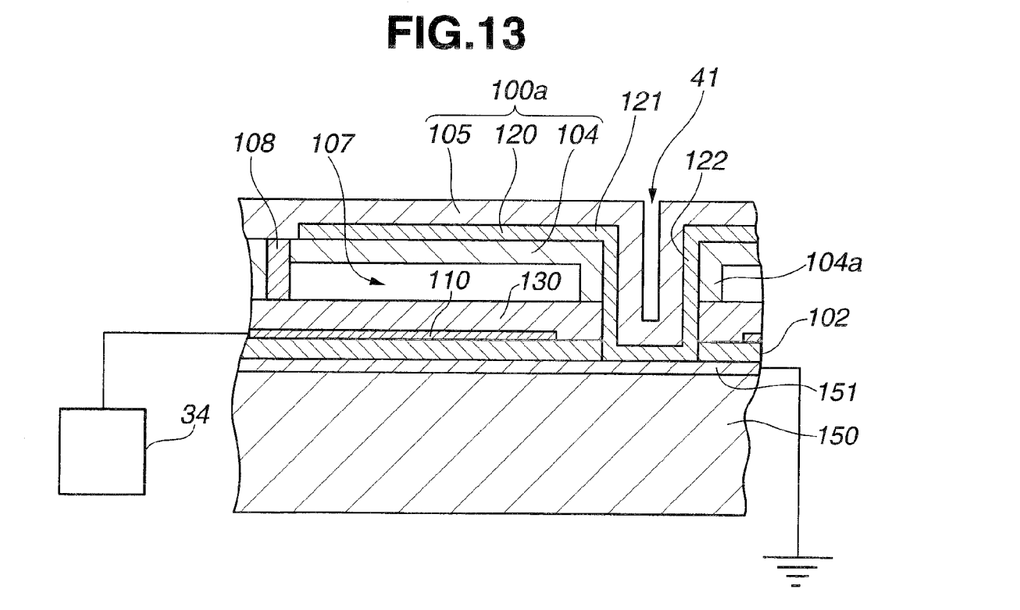
FIG. 13 is a sectional view of a transducer cell according to a fourth embodiment.

A fourth embodiment of the present invention will be described below with reference to FIG. 13. FIG. 13 is a sectional view of a transducer cell according to the fourth embodiment. The fourth embodiment is different from the configuration in the first embodiment in a material for a substrate on which a transducer cell is to be formed. Thus, only the difference will be described below. Same components as the components in the first embodiment are denoted by same reference numerals, and a description of the components will be appropriately omitted.

In the present embodiment, the transducer cell is formed on an insulative substrate 150 made of quartz, which is electrically insulative. The insulative substrate 150 is not limited to quartz and may be made of an insulative material such as sapphire, crystal, alumina, zirconia, glass, or resin.

On a surface of the insulative substrate 150, a ground conductive layer 151 which is a metal film is formed as a conductive processing portion which makes the surface of the insulative substrate 150 conductive, by forming a film of a conductive material such as Mo by sputtering. Note that the ground conductive layer 151 may have a multilayered structure in which two or more types of conductive materials are stacked. For example, the ground conductive layer may be composed of two-layer metal films, a lower one of the layers (one in contact with the ground conductive layer 151) may be made of any of Cr, Ni, Cu, Ti, and Sn, and an upper one of the layers may be made of any of Pt, Au, W, Mo, and Ta.

The ground conductive layer 151 is set to a ground potential, and a configuration same as the configuration of the transducer cell 100 according to the first embodiment is stacked on the ground conductive layer 151. That is, the transducer cell according to the present embodiment is equivalent to a configuration obtained by replacing the silicon substrate 101 according to the first embodiment with the ground conductive layer 151 in terms of an electric circuit and is an equivalent circuit same as the equivalent circuit in the first embodiment.

In the transducer cell according to the present embodiment, a back surface of the insulative substrate 150 is fixed on a FPC with adhesive agent or the like and is then electrically connected to a wiring pattern of the FPC by wire bonding or the like. With the configuration, the ground conductive layer 151 and a lower electrode 110 are electrically connected to the ground potential and a control circuit 34, respectively.

According to the present embodiment, it is possible to suppress generation of parasitic capacitance which is generated when a conductive substrate is used as wiring and more efficiently control driving of a transducer cell, as compared with a case where a transducer cell is formed on a conductive substrate.

Note that the present invention is not limited to the above-described embodiments, and changes may be appropriately made without departing from scope and spirit of the present invention which can be read from the claims and the entire specification. An ultrasound transducer and an ultrasound diagnostic apparatus involving such changes are also included in technical scope of the present invention.

For example, in the above-described embodiments, the ferroelectric film is disposed to overlap the transducer cell when viewed from above, i.e., to be stacked on the transducer cell. A position where the ferroelectric film is provided is not limited to this. For example, the transducer cell and the ferroelectric film may be disposed to be spaced apart from each other when viewed from above.

The ultrasound endoscopes have been described as performing electronic radial scanning and sector scanning. However, a scanning system is not limited to this, and linear scanning, convex scanning, or the like may be adopted. The ultrasound transmission/reception portion may be composed of a one-dimensional array in which a plurality of transducer elements are one-dimensionally arrayed. Additionally, the present invention can also be applied to an ultrasound endoscope of a mechanical scanning system. The present invention can be applied not only to an endoscope in the above-described form having transducer elements arranged in an array but also to an endoscope using a single transducer element.

The present invention belongs to a technical field including not only an endoscope having an ultrasound transmission/reception portion at a distal end but also a so-called ultrasound probe in general which is introduced into a body cavity regardless of whether the ultrasonic probe uses a wired system or a wireless system. For example, the present invention may relate to an ultrasound probe which is inserted through a treatment instrument insertion hole of an endoscope and is introduced into a body cavity.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An ultrasound transducer of a capacitance type comprising:
    a first electrode which is disposed on a substrate and applied with a driving signal which is a voltage signal of which polarity is reversed every time the driving signal is applied;
    a vibration film which is disposed above the first electrode with an air and vacuum portion between the vibration film and the first electrode;
    a second electrode which is disposed on the vibration film and is set to a ground potential; and
    a ferroelectric which is electrically connected to the first electrode and has spontaneous polarization whose polarity is reversed by a given electric field.

2. The ultrasound transducer according to claim 1, wherein the ferroelectric is disposed between the substrate and the first electrode.

3. The ultrasound transducer according to claim 1, wherein the ferroelectric is disposed between the first electrode and the air and vacuum portion.

4. The ultrasound transducer according to claim 1, comprising a driving portion that applies the driving signal to the first electrode.

5. The ultrasound transducer according to claim 1, wherein the substrate is made of an electrically insulative material and is an insulative substrate having a conductive processing portion with conductivity disposed on a surface, and the conductive processing portion is set to the ground potential.

6. The ultrasound transducer according to claim 5, wherein the conductive processing portion is at least one layer of a metal film disposed on the insulative substrate.

7. The ultrasound transducer according to claim 5, wherein the conductive processing portion is composed of two-layer metal films disposed on the insulative substrate, and one metal film of the two-layer metal films which is disposed on the insulative substrate side is made of any one of Cr, Ni, Cu, Ti, and Sn, and the other metal film is made of any one of Pt, Au, W, Mo, and Ta.

8. The ultrasound transducer according to claim 1, wherein the substrate is a low-resistivity substrate which is made of a conductive material, and the low-resistivity substrate is set to the ground potential.

9. The ultrasound transducer according to claim 8, wherein the low-resistivity substrate is made of a silicon semiconductor.

10. The ultrasound transducer according to claim 4, wherein the substrate is a low-resistivity substrate made of silicon semiconductor and at least a part of the driving portion is formed on the silicon semiconductor.

11. The ultrasound transducer according to claim 1, wherein the ferroelectric is made of a bismuth layer structured ferroelectric.

12. An ultrasound diagnostic apparatus comprising the ultrasound transducer according to claim 1.

13. The ultrasound transducer according to claim 1, wherein the driving signal is a monopulse voltage signal.

* * * * *